US008323349B2

(12) United States Patent
Schmid

(10) Patent No.: US 8,323,349 B2
(45) Date of Patent: Dec. 4, 2012

(54) TEXTURED SURFACES FOR ORTHOPEDIC IMPLANTS

(75) Inventor: Steven R. Schmid, Lakeville, IN (US)

(73) Assignee: The University of Notre Dame Du Lac, Notre Dame, IN (US)

( * ) Notice: Subject to any disclaimer, the term of this patent is extended or adjusted under 35 U.S.C. 154(b) by 500 days.

(21) Appl. No.: 11/060,377

(22) Filed: Feb. 17, 2005

(65) Prior Publication Data

US 2005/0182494 A1 Aug. 18, 2005

Related U.S. Application Data

(60) Provisional application No. 60/544,334, filed on Feb. 17, 2004.

(51) Int. Cl.
*A61F 2/34* (2006.01)
(52) U.S. Cl. .................................................. 623/23.58
(58) Field of Classification Search .... 623/22.13–22.19, 623/17.12, 17.15, 20.26, 20.27, 20.33, 21.17, 623/36, 23.5–23.59, 23.3
See application file for complete search history.

(56) References Cited

U.S. PATENT DOCUMENTS

| | | | | |
|---|---|---|---|---|
| 3,662,405 A * | 5/1972 | Bortz et al. | ................ | 623/23.51 |
| 3,683,421 A * | 8/1972 | Martinie | ................ | 623/22.13 |
| 4,156,943 A * | 6/1979 | Collier | ................ | 623/23.55 |
| 5,092,898 A * | 3/1992 | Bekki et al. | ................ | 623/22.16 |
| 5,514,182 A * | 5/1996 | Shea | ................ | 623/23.4 |
| 5,537,851 A * | 7/1996 | Sheu et al. | ................ | 72/366.2 |
| 5,549,700 A * | 8/1996 | Graham et al. | ................ | 623/22.14 |
| 5,641,323 A * | 6/1997 | Caldarise | ................ | 623/22.18 |
| 5,879,406 A * | 3/1999 | Lilley | ................ | 623/22.15 |
| 5,989,250 A | 11/1999 | Wagner et al. | | |
| 6,290,726 B1 * | 9/2001 | Pope et al. | ................ | 623/22.15 |
| 6,425,921 B1 * | 7/2002 | Grundei et al. | ................ | 623/22.15 |
| 6,494,916 B1 * | 12/2002 | Babalola et al. | ................ | 623/23.3 |
| 6,547,824 B1 * | 4/2003 | Price | ................ | 623/18.11 |
| 6,610,095 B1 * | 8/2003 | Pope et al. | ................ | 623/18.11 |
| 6,660,040 B2 * | 12/2003 | Chan et al. | ................ | 623/22.21 |
| 6,709,464 B2 * | 3/2004 | Scott et al. | ................ | 623/23.58 |
| 2001/0039455 A1 * | 11/2001 | Simon et al. | ................ | 623/23.51 |
| 2002/0022884 A1 * | 2/2002 | Mansmann | ................ | 623/14.12 |
| 2002/0035400 A1 * | 3/2002 | Bryan et al. | ................ | 623/17.15 |
| 2002/0128715 A1 * | 9/2002 | Bryan et al. | ................ | 623/17.15 |
| 2002/0143402 A1 * | 10/2002 | Steinberg | ................ | 623/22.16 |
| 2002/0183850 A1 * | 12/2002 | Felt et al. | ................ | 623/20.16 |
| 2003/0060891 A1 * | 3/2003 | Shah | ................ | 623/22.13 |

(Continued)

OTHER PUBLICATIONS

Aspinwall, et al. "Electrical Discharge Texturing" *Int. J. Mach. Tools Man.*, 32, (1992), pp. 183-193.

(Continued)

*Primary Examiner* — Eduardo C Robert
*Assistant Examiner* — Ann Schillinger
(74) *Attorney, Agent, or Firm* — Kilpatrick, Townsend & Stockton, LLP.

(57) ABSTRACT

A bearing surface having increased wear resistance. Generally, certain aspects of the present invention are directed to an implant design based on concepts of unidirectional load application and the use of engineered surfaces to increase the amount of lubricant at the bearing surface, to thereby reduce wear of the bearing surface. Surfaces of certain bearing surface embodiments are fabricated to maximize lubricant retention, encourage lubricant entrainment, and/or restrict lubricant escape from the bearing surface. Preferably, when used in orthopedic applications, such bearing surfaces are optimized based on the unique characteristics of human biomechanical loading.

50 Claims, 8 Drawing Sheets

U.S. PATENT DOCUMENTS

2003/0097182 A1* 5/2003 Buchman et al. ......... 623/18.11
2003/0114934 A1* 6/2003 Steinberg ................. 623/22.17
2003/0130743 A1* 7/2003 Scott et al. ............... 623/23.58

OTHER PUBLICATIONS

Aspinwall, et al. "Electrodischarge Texturing (EDT) of Steel Rolls", *Surface Topography*, 2. (1989), pp. 123-141.

Bergmann, et al. "Influence of Shoes and Heel Strike on the Loading of the Hip Joint", *J. Biomechanics*, 28, (1995), pp. 817-827.

Blunn, et al. "Polyethylene Wear in Unicondylar Knee Prosthesis" *Acta Orthop. Scand.*, 63, (1992), pp. 247-255.

Boppel, W. "A Rapid Electron Beam Engraving Process for Engraving Metal Cylinders" *Optik*, 77, (1987), pp. 83-92.

Collier, et al. "Analysis of the Failure of 122 Polyethylene Inserts from Uncemented Tibial Knee Components" *Clin. Orthop. Rel. Res.*, 273, (1991), pp. 232-242.

Dolves, J. "Electron Beam Texturing of Rolls" *Iron and Steel Eng.*, 68, (1991), pp. 33-38.

Hector, et al. "Focused Energy Beam Work Roll Surface Texturing Science and Technology" *J. Mat. Proc. & Mfg. Sci.*, 2, (1993), pp. 63-117.

Landy, et al. "Wear of Ultra-High-Molecular-Weight Polyethylene Components in 90 Retrieved Knee Prostheses" *J. Arthroplasty*[Suppl.], 3, (1988), pp. S73-S85.

Lo. S. "A Study of Flow Phenomena in Mixed Lubrication Regime by Porous Media Model" *J. Tribology*, 116, (1994), pp. 640-647.

McGeough, et al. "A Model for the Surface Texturing of Steel Rolls by Electrodischarge Machining" *Proc. Roy. Soc. Lond., Ser.* A, v. 436, (1992), pp. 155-164.

Minamida, et al. "Laser System for Dulling Work Roll by Q-Switched Nd:YAG laser" *J. Laser Appls.*, 1, (1989). pp. 15-20.

Patir, et al. "Effect of Surface Roughness on the Central Film Thickness in EHD Contacts" *Elastohydrodynamics and Related Topics*, Proceedings of the Fifth Leeds-Lyon Symposium on Tribology, Institution of Mechanical Engineers, London, (1978), pp. 15-21.

Sheu, et al. "Tool Surface Topographies for Controlling Fiction and Wear in Metal-Forming Processes" *J. Tribology Sci.*, 120, (1998), pp. 517-527.

Smith, et al. "The Lubrication of Metal-On-Metal Total Hip Joints: a Slide Down the Stribeck Curve" *Proc. Inst. Mech. Eng. Pt. J: J Engineering Tribology*, 215, (2001), pp. 483-493.

Taylor, S.J.G. "Forces and Moments Telemetered From Two Distal Femoral Replacements During Various Activities" *J. Biomechanics*, 34, (2001), pp. 839-848.

Unsworth, et al. "The Frictional Behavior of Human Synovial Joints: Part 1—Natural Joints" *J. Lubr. Tech.*, F97, (1975), pp. 369-376.

Communication pursuant to Article 94(3) EPC, EP Application No. 04818642.3, mailed Jun. 25, 2010, 6 pages.

* cited by examiner

Boundary film

Bulk lubricant (a)

(b)

(c)

$\gamma = 6$ $\gamma = 1$ $\gamma = 1/6$

TEXTURED SURFACES FOR ORTHOPEDIC IMPLANTS

RELATED APPLICATIONS

This application claims the benefit of and priority to U.S. Provisional Patent Application No. 60/544,334, filed on Feb. 17, 2004, the entirety of this application is hereby incorporated herein by reference.

BACKGROUND

1. Field of the Invention

The present invention relates generally to surface texturing and, more particularly, to surface texturing of orthopedic implants.

2. Related Art

With the great advances in medical care in the past few decades, life expectancies have been considerably increased. With these advances have come additional expectations that the quality of life in later years will remain high. Senior citizens enjoy an active lifestyle. The confinement of the elderly to wheelchairs or immobile lives, common just a generation ago, is now considered unacceptable.

One of the reasons for the realized improvements in quality of life of the elderly has been the great success of orthopedic implants in the past forty years. Hip, knee, shoulder, spine and other implants have resulted in increased activity and reduced pain for millions of people worldwide.

However, orthopedic implants have a limited life, with modern hip or knee implants having a useful life of between 15 and 20 years. Many factors contribute to the limited lifespan of orthopedic implants including, for example, fatigue failure, corrosion and, most commonly, wear or osteolyses (bone weakening) due to a biological response to wear particles. Recognizing this, implant manufacturers have developed superior polymers, such as highly crosslinked ultra-high molecular weight polyethylene, and more recently, new tribological material pairs, such as ceramic-on-ceramic and metal-on-metal implants. Such advances have not eliminated the ultimate requirement to replace the initial implant with a revision implant.

Unfortunately, revision implants are often found to be far more problematic than initial implants from a medical and rehabilitation standpoint. For example, more bone and soft tissue trauma are encountered than in initial implants, pain is greater and rehabilitation is longer. Any technology that extends the life of an orthopedic implant would be welcomed by physicians and patients alike.

SUMMARY

In one aspect of the invention, an apparatus comprising a textured bearing surface is disclosed. The texture bearing surface has a predetermined pattern of asperities constructed and arranged to encourage lubricant entrainment while the bearing surface is under minimal loading, and to restrict lubricant escape from the bearing surface while the bearing surface is under increased loading.

In another aspect of the invention, an apparatus comprising a textured bearing surface is disclosed. The texture bearing surface has an predetermined pattern of indentations and surrounding plateaus, each indentation containing at least one surface that contains a substantially smooth transition to the plateau and whose concavity is zero at the junction with the plateau surface.

In a further aspect of the invention, an apparatus comprising a textured bearing surface is disclosed. The texture bearing surface has a predetermined pattern of asperities constructed and arranged to increase lubricant retention, encourage lubricant entrainment and restrict lubricant escape from the bearing surface.

BRIEF DESCRIPTION OF THE DRAWINGS

FIG. 3A is a Stribeck curve showing the relationship between friction and film parameter, with similar behavior seen for wear; and FIG. 3B is a graph showing bearing life as a function of film parameter.

FIG. 4A shows the definition of the surface pattern parameter, in which the ellipses represent the areas of contact between two surfaces and are indicative of the directionality or lay of the surface and the sliding or rolling direction is horizontal; and with FIG. 4B showing film thickness generated as a function of surface pattern parameter.

FIGS. 6A and 6B show examples of laser textured surface profiles, in which FIG. 6A shows a hexagonal pattern, and FIG. 6B shows details of a crater.

DETAILED DESCRIPTION

Figure 1:
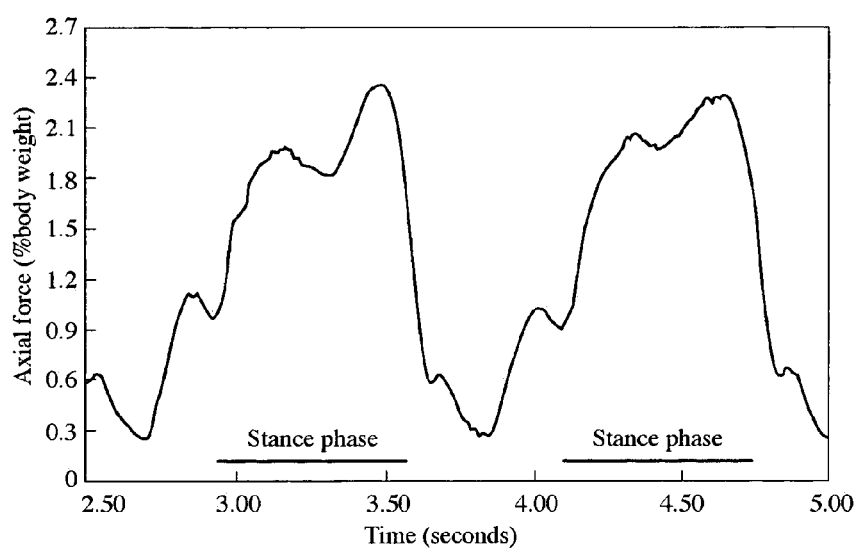
FIG. 1 is a graph illustrating axial loads measured on a human implant in a 41 year old female one year after implantation.

Aspects of the present invention are directed to bearing surfaces having increased war resistance. Generally, certain aspects of the present invention are directed to an implant design based on concepts of unidirectional load application and the use of engineered surfaces to increase the amount of synovial fluid at the bearing surface, to thereby reduce wear in the implant. Surfaces of certain implant embodiments are fabricated to maximize lubricant retention, encourage lubricant entrainment, and restrict lubricant escape from the bearing surface. Preferably, such bearing surfaces are optimized based on the unique characteristics of human biomechanical loading.

More specifically, aspects of the present invention are directed to the design of reciprocating or articulating surfaces of an orthopedic implant to optimize lubricant retention and wear resistance of such surfaces, even during, for example, unsteady and repetitious loading. Most orthopedic implants (hips, knees, spine disk replacements, etc.) share many characteristics. For example, the bearing or wear surfaces of orthopedic implants are traditionally produced from abrasive machining processes such as grinding and polishing, leading to a smooth surface with a predominantly linear lay of the surface asperities. Also, orthopedic implants commonly experience an unsteady loading when in use. That is, there is significant loading in one sliding direction (as in the stance phase of walking) followed by return sliding under much lower loads (the swing stage of walking). Another common characteristic of many orthopedic implants is that wear particles are inevitably introduced; these can be foreign particles originating from the human body, the implant or bone cement, or foreign particles in the form of an embedded slurry particle residue produced during the polishing process, etc. It is well understood that such wear particles can cause far more damage than normal surface interactions. Furthermore, there is a fluid surrounding the joint; that is, the interface between the bearing surfaces. This fluid, commonly referred to as synovial fluid, which is predominantly water with some suspended proteins. All implants are lubricated to some extent by the synovial lubricant.

In some embodiments the bearing surface of the orthopedic implant is textured. Such texture can be provided by forming localized indentations or bumps on the surface. In the embodiments described herein, the textured surface is provided by forming a number of dimples on the surface. As will be described in detail below, textured surfaces such as the dimpled surfaces disclosed herein provide superior lubrication and wear resistance. Specifically, the dimples improve lubricant retention by the surfaces and also accommodate wear particles without damaging the surfaces.

In accordance with the teachings of the present invention, the texture is formed by a predetermined arrangement of, for example, dimples. The predetermined or engineered surfaces may be produced through a variety of techniques now or later developed, including laser texturing, chemical etching, plasma etching, electrical discharge machining, electron beam machining, peening, etc. In the embodiments described herein, laser texturing is described for illustrative purposes only. It should be understood by one of ordinary skill in the art that other suitable surface processing methods now or later developed may be utilized.

In certain embodiments of the present invention, dimples are placed on the surface of an implant in a density and orientation that are optimized for a particular biomechanical loading. During the loading or stance phase, the leading edge of the dimple is designed to maximize lubricant retention, for example, by minimizing lubricant flow. During the reduced-load or swing stage, the leading edge of the dimple is designed to maximize lubricant flow to encourage lubricant entrainment.

In certain embodiments, the indentations or dimples are oriented so that they present a trailing edge having a very small slope when sliding takes place under load (for example, during the stance phase of walking for hip, knee, spine disk replacement and other orthopedic implants). In one embodiment, ovoid dimples are formed in the implant surface.

Biomechanics of Walking and Human Joints. The human knee and hip joints have unique characteristics and loadings. When walking, load is applied in directional sliding in one direction, but the return of the joint to the start position is under much lower load, applied only through tendon and muscle. That is, sliding in the stance phase of walking is under load, while under the swing phase it is under very low (perhaps negligible) load. The load on the hip or any other articulating surface including all orthopedic joints is not steady, an unusual but not unheard of circumstance in tribological applications. Similar loadings and kinematics occur in a number of bearings such as piston main bearings and reciprocating cams. However, the inventor has discovered that there is an opportunity to develop a large film during the swing stage and then maintain that film during the stance stage of walking.

FIG. 1 shows the measured forces on an artificial implant, as measured with an encapsulated strain gage, see Taylor, S. J. G., "Forces and moments telemetered from two distal femoral replacements during various activities," *J. Biomechanics*, v. 34, 2001, pp. 839-848, the entire contents and disclosure of which is hereby incorporated by reference herein. It has also been reported in Bergmann, G., Kniggendorf, H., Graichen, F., and Rohlmann, A., "Influence of shoes and heel strike on the loading of the hip joint," *J. Biomechanics*, v. 28, 1995, pp. 817-827, the entire contents and disclosure of which is hereby incorporated by reference herein, that the peak load may be as high as 350% of body weight, and that during the swing phase the normal load is reduced to around zero. This is consistent with the tactile experience of all humans.

It should be noted that an orthopedic implant presents a tribological condition that is typically less suitable than the natural joint. The reasons are many, but this is mostly because the artificial implant does not heal, and wear particles may lead to further inflammation. Cartilage may heal under some circumstances, and cartilage wear particles do not result in osteolyses. Also, the hardness mismatch in metal-on-polymer implants makes the polymer a sacrificial element; it wears preferentially to the metal.

As noted, synovial fluid is present in all joints. All tribological contacts, including natural and artificial joints, are subject to extremely high shear stresses and strains, which is sufficient to shear and blend biological soft tissue, blood and fluids that are entrained in joints. The rheological properties of the resulting synovial fluid vary greatly from patient to patient, but it has been noted that synovial fluid may have superior lubricating properties. While the fluid in the joint is one of the most advantageous tribological parameters in natural and artificial joints, exploitation of this fluid has attracted only limited attention of orthopedic implant designers to date.

Figure 2:
FIG. 2 includes three panels each illustrating a different regime of lubrication, in which panel (a) shows full film lubrication, sometimes further classified into thin and thick film regimes; panel (b) shows mixed or partial lubrication; and panel (c) shows boundary lubrication.
Figure 2:
Figure 2:
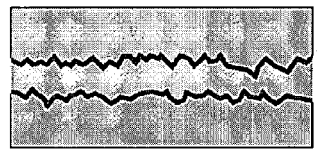
Figure 2:
Figure 2:
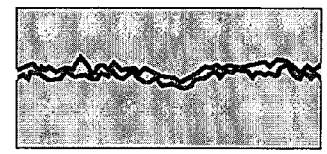

Regimes of Lubrication. To understand the value of the various aspects of the present invention, some fundamental tribological concepts should be briefly reviewed and placed in the context of orthopedic implants. One of the most fundamental concepts of lubricated conjunctions is that of regimes of lubrication, illustrated in FIG. 2, and discussed in practically any modern tribology textbook. See, for example Hamrock, et al., *Fundamentals of Fluid Film Lubrication*, New York, McGraw-Hill, 2004; Bhushan, B., *Introduction to Tribology*, New York, Wiley & Sons, 2002; and Szeri, A. Z., *Fluid Film Lubrication*, Cambridge, Cambridge University Press, 1998, the entire contents and disclosures of which are hereby incorporated by reference herein. The construct of lubrication regimes describes the media through which load is transferred between bearing surfaces, whether through a pressurized lubricant film, through opposing surface asperities or through a combination of these effects. The regimes of lubrication are commonly defined through a film parameter, Λ. The term "film parameter" generally refers to the ratio of the mean film thickness to the root-mean-square composite roughness of two contacting surfaces, as defined in Equation (1) below:

$$\Lambda = \frac{h}{\sqrt{R_{qa}^2 + R_{qb}^2}} = \frac{h}{\sigma} \quad (1)$$

where h is the film thickness, $R_{qa}$ and $R_{qb}$ are the surface roughness of the two contacting surfaces, and s is the composite roughness.

If Λ is less than one (1), it is generally considered to be a circumstance of boundary lubrication. As used herein, the term "boundary lubrication" refers to the situation where two surfaces in contact with each other (1) transmit load substantially through asperities in direct contact through a film of molecular dimensions, known as a boundary film or (2) transmit load substantially directly through the solid asperities. In either case, a lubricant may exist in the valleys of the surfaces in contact, but it does not transfer appreciable load. This is illustrated in panel (c) of FIG. 2.

If Λ is greater than approximately three (3), then full film lubrication occurs, where the load between asperities is transferred across a pressurized lubricant, and asperities are rarely in contact. As used herein, the term "full film lubrication" refers to a lubricated contact where the two opposing surfaces are substantially separated by a lubricant film. Sometimes, full film lubrication is separated into two regimes, that of thin film (where $3 \leq \Lambda \leq 10$) and that of thick film ($\Lambda \geq 10$), although this distinction is not particularly useful for orthopedic implants. This is illustrated in panel (a) of FIG. 2.

If Λ is between one (1) and three (3), then the load between surfaces is shared by lubricant and asperities and is referred to as mixed or partial lubrication. As used herein, the terms "mixed lubrication" and "partial lubrication" each refer to the situation where load is transferred between two contacting surfaces through the substantially simultaneous action of a pressurized lubricant film and asperities in direct contact. This is illustrated in panel (b) of FIG. 2.

Natural joints experience boundary, mixed or full-film or hydrodynamic films at different times and loads. See, for example, Dowson, D., *History of Tribology, 2nd ed.*, London, Professional Engineering Publishing, 1998, pp. 508-509; Unsworth, A., Dowson, D., and Wright, V., "The frictional behavior of human synovial joints: Part I—Natural Joints", *J. Lubr. Tech.*, v. F97, 1975, pp. 369-376; and Smith, S. L., Dowson, D., and Goldsmith, A. A. J., "The lubrication of metal-on-metal total hip joints: a slide down the Stribeck curve", *Proc. Inst. Mech, Eng. Pt. J: J. Engineering Tribology*, v. 215, 2001, pp. 483-493, the entire contents and disclosures of which are hereby incorporated by reference herein.

Most orthopedic implants operate within the boundary or mixed lubrication regimes, although some evidence exists that modern ceramic implants achieve full films by reducing the surface roughness in Equation (1). Metal-on-metal and metal-on-plastic designs operate in the partial or boundary lubrication regimes. The lubrication regime is dependent on the head size with hips, with larger heads leading to thicker films and less wear, see Smith, S. L., Dowson, D., and Goldsmith, A. A. J., "The lubrication of metal-on-metal total hip joints: a slide down the Stribeck curve", *Proc. Inst. Mech, Eng. Pt. J: J. Engineering Tribology*, v. 215, 2001, pp. 483-493, the entire contents and disclosure of which is hereby incorporated by reference herein. Of course, there is a limit to the size of implants that may be placed in the human body.

Figure 3A:
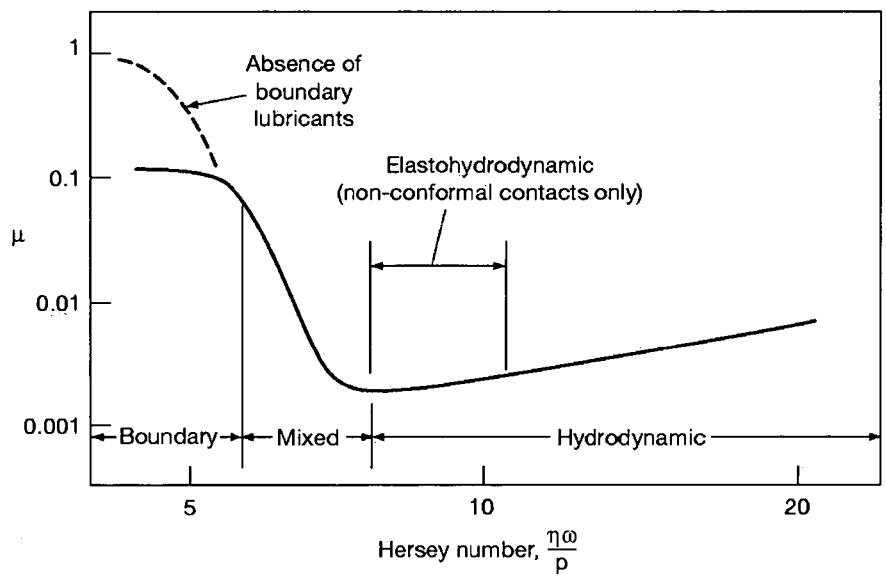
FIGS. 3A and 3B are graphs illustrating the effects of film parameters on tribological performance, where
Figure 3B:
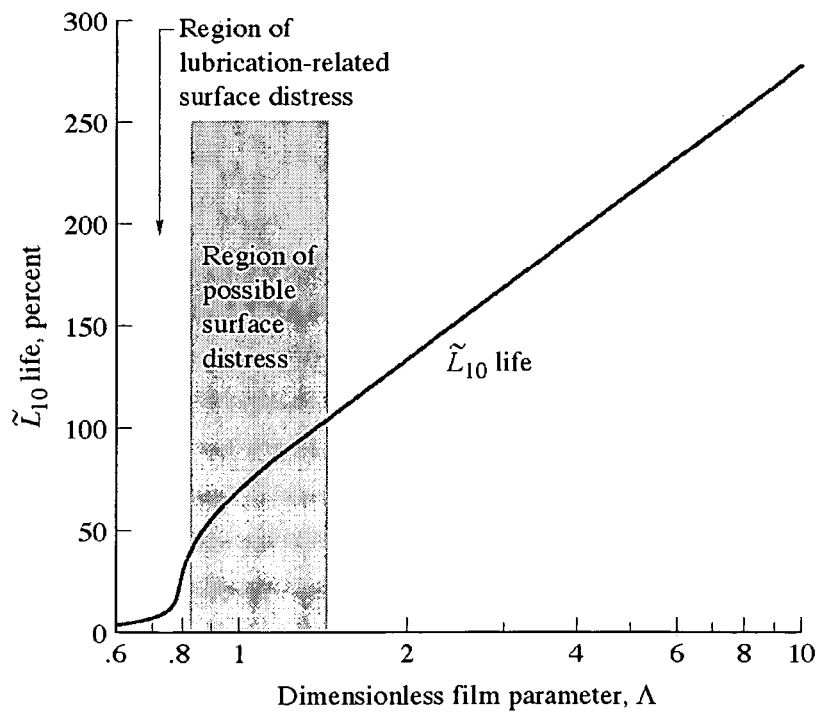

FIGS. 3A and 3B are graphs illustrating the effects of film parameters on tribological performance, where FIG. 3A is a Stribeck curve showing the relationship between friction and film parameter, with similar behavior seen for wear; and FIG. 3B is a graph showing bearing life as a function of film parameter. From FIGS. 3A and 3B, the inventors determined that the lubricant film thickness plays a role in wear in the mixed lubrication regime, and that small increases in the film thickness (and hence film parameter) may lead to large decreases in wear rates.

It is well-known that the local surface angle of the asperities plays a large role in abrasive wear. Sharp asperities will likely penetrate into a softer opposing material and plow through it, causing pure elastic deformation and recovery of the softer material; plastic deformation and the generation of a groove in the softer material; and/or generation of a chip or wear particle in the softer material. Smooth surfaces, that is, surfaces with small slopes, are less likely to generate wear particles through abrasion. For this reason, the local slope of the surfaces is often one of the factors considered when attempting to control abrasive wear.

It should be noted that wear is a complex phenomenon, and there are many types of wear. Walker and Blunn summarized clinical findings for retrieved artificial joints, and found that three types of wear occur in orthopedic implants. See Walker, P. S., and Blunn, G. W., "Biomechanical Principles of Total Knee Replacement Design," Chapter 12 in Mow, V. C., and Hayes, W. C., eds., *Basic Orthopedic Biomechanics, 2nd ed.* Philadelphia, Lippencroft-Raven Publishers, 1997, pp. 461-493; Blunn, G. W., Joshi, A. B., Lilley, P. A., et al., "Polyethylene wear in unicondylar knee prostheses," *Acta Orthop. Scand.*, v. 63, 1992, pp. 247-255; Collier, J. P. M., Mayor, M. B., McNamara, J. L., Surprenant, V. A., and Jenson, R. E., "Analysis of the failure of 122 polyethylene inserts from uncemented tibial knee components," *Clin. Orthop. Rel. Res.*, v. 273, 1991, pp. 232-242; and Landy, M. M., and Walker, P. S., "Wear of ultra-high-molecular-weight polyethylene components in 90 retrieved knee prostheses," *J. Arthroplasty [Suppl.]*, v. 3, 1988, pp. S73-S85, the entire contents and disclosures of which are hereby incorporated by reference herein. Adhesive wear, occurring at local contact points between metal and polymer, created particles and shreds between 0.1 and 10 μm in size. Abrasive wear, either two body (from a hard point on the metal surface) or three body (from a wear particle or cement particle trapped in the contact) occurs due to cutting of the polymer surface. Delamination or fatigue wear occurs due to subsurface cracks coalescing and propagating to the surface.

FIGS. 3A and 3B present data for friction and fatigue wear as a function of the above-noted film parameter. Similar effects may be found for adhesive and abrasive wear, although some mechanisms particular to each case should be discussed. A lubricant film has the beneficial effect of separating the surfaces, practically eliminating adhesion, microwelding between asperities and adhesive wear. The effects of a lubricant film on adhesive wear is thus fairly straightforward.

With abrasive wear, it should be realized that increasing the film parameter given by Equation (1), either by increasing the film thickness h or decreasing the composite roughness s, leads to less intimate surface interaction in the boundary or mixed lubrication regimes. This results in smaller penetration depths by the harder asperities into the softer material, and makes abrasive wear much less severe.

In fatigue wear, lubricant films play an important role because they reduce the maximum stress encountered by the materials and also reduce surface tractions because of friction reduction.

It should be recognized that an increase in the film parameter Λ may lead to a reduction in wear rates for all wear mechanisms, and especially in the boundary and mixed regimes ($\Lambda \leq 3$).

Figure 4A:
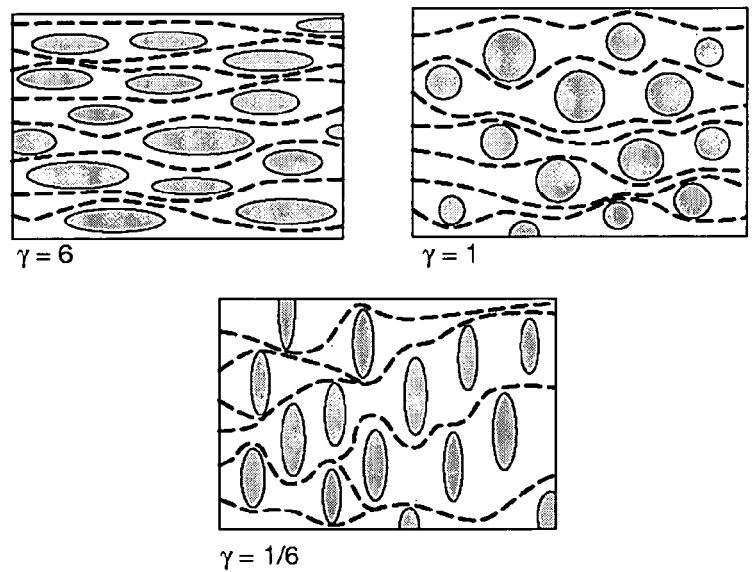
FIGS. 4A and 4B show the effects of surface roughness on film thickness in mixed lubrication, where
Figure 4B:
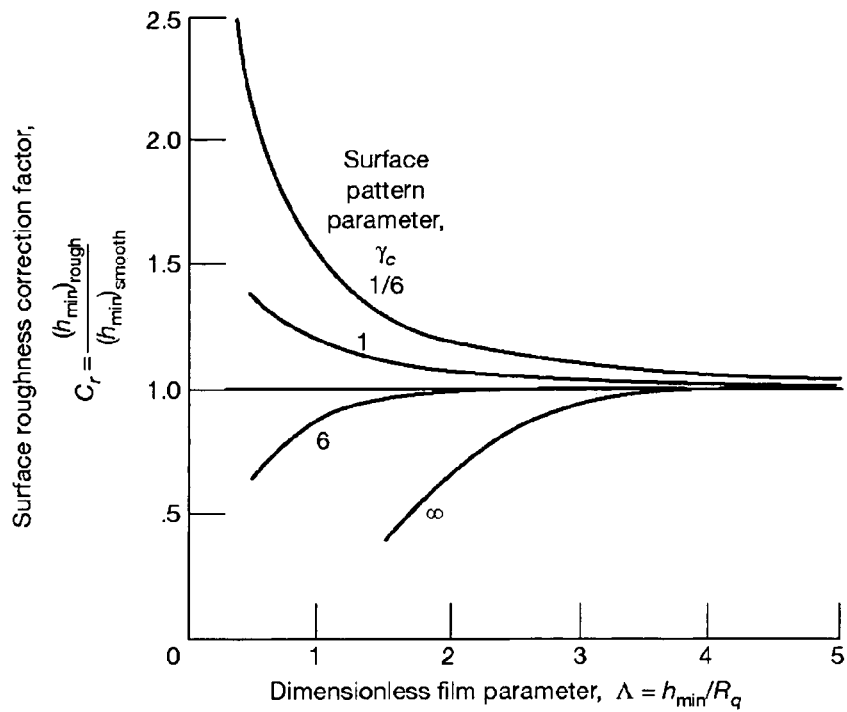

Surface Roughness Effects on Film Thickness. In a landmark paper, Patir and Cheng developed the theory for surface roughness effects on entrained lubricant film thickness, Patir. and Cheng, H. S., "Effect of surface roughness on the central film thickness in EHD contacts," *Elastohydrodynamics and Related Topics*, Proceedings of the Fifth Leeds-Lyon Symposium on Tribology, Institution of Mechanical Engineers, London, 1978, pp. 15-21, the entire contents and disclosure of which is hereby incorporated by reference herein. Their results are shown in FIGS. 4A and 4B, which show that the film thickness for rough surfaces with a proper orientation may be much larger than for smooth surfaces, especially in the mixed film and boundary regimes. The Peklenik or surface pattern parameter γ shown in FIGS. 4A and 4B is defined as the ratio of autocorrelation lengths of the surface in the sliding and transverse directions; see Hamrock, B. J., *Fundamentals of Fluid Film Lubrication*, New York, McGraw-Hill, 1994, the entire contents and disclosure of which is hereby incorporated by reference herein.

From the above and other observations, the inventors concluded that when the roughness is directionally oriented perpendicular to the sliding direction, a larger film thickness may be entrained. To maximize film thickness development in the swing stage of walking, there is preferably minimal restriction to lubricant entrainment. FIGS. 4A and 4B show the effects of surface roughness on film thickness in mixed lubrication, where FIG. 4A shows the definition of the surface pattern parameter, in which the ellipses represent the areas of contact between two surfaces and are indicative of the directionality or lay of the surface and the sliding or rolling direction is horizontal; and with FIG. 4B showing film thickness generated as a function of surface pattern parameter.

From FIGS. 4A and 4B, this would suggest using surface asperities oriented in the direction of sliding, or high γ. To maximize film thickness retention during the stance phase there should provide maximum resistance to outflow of lubricant. From FIGS. 4A and 4B, this suggests using surface asperities oriented perpendicular to the direction of sliding. These contradictory requirements explain why conventional ground or polished surfaces do not yield favorable results with respect to surface-affected lubricant entrainment. Also, since ground and polished surfaces are the best practice currently available, it is the practice of implant manufacturers to provide very smooth surfaces for knees or hip balls, so that a given film thickness leads to a maximum film parameter (see Equation (1)).

Figures 5A, 5B:
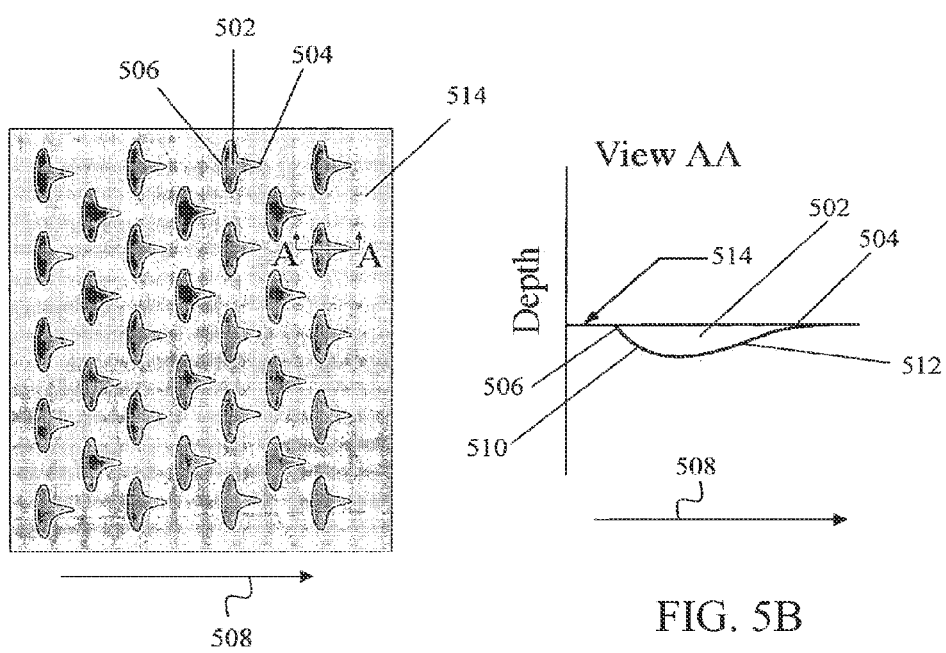
FIGS. 5A and 5B are sketches of a surface pattern according to an embodiment of the present invention.

It should be recognized that Patir and Cheng developed their theory for Gaussian (random) surfaces, which is a reasonable approximation for ground or machined surfaces common in bearings. However, surface textures of the present invention are not Gaussian, facilitating significant modification of lubricant entrainment in a directional manner. For example, in the embodiment shown in FIGS. 5A and 5B, the dimples 502 have a profile that encourages entrainment for sliding in one direction 512 as shown by arrow 508, but provides less restriction to lubricant flow in the opposite direction 510. A matrix or pattern consisting of such dimples 502 presents a superior surface 514. While such surfaces are interesting from an academic standpoint, they are difficult to manufacture, since the surface features preferably have a depth that is on the order of the film thickness, or around 50 to 100 microns.

However, it should be realized that in those embodiments in which the implemented surface texture is purposefully designed to entrain lubricant during walking has the following benefits: (1) the film thickness developed during the swing stage is larger; (2) the surface restricts outflow of lubricant during the stance stage, so that the film thickness during walking is larger; (3) during standing, the fluid eventually is squeezed out of the joint until boundary lubrication is achieved; however, since there is little relative motion between the surfaces, wear is minimal. As soon as walking is initiated, a thicker film is developed than with untreated surfaces; and (4) beneficial engineered surfaces may not be manufactured through conventional grinding or polishing operations.

Textured Surfaces. A number of techniques for texturing tribological surfaces exist and have been investigated, including electrical discharge texturing, electron beam texturing, plastic deformation, as well as attempts at using Nd:YAG lasers and $CO_2$ lasers for texturing, marketed in Europe under the trade name LASERTEX (see www.lasertex.de), see also Aspinwall, D. K., Zhao, F. L., and El-Menshawy, M. F., "Electrodischarge texturing (EDT) of steel rolls", *Surface Topography*, v. 2, 1989, pp. 123-141; Aspinwall, D. K., Wise, M. L. H., Stout, K. J., Goh, T. H. A., Zhao, F. L., and El-Menshawy, M. F., "Electrical discharge texturing," *Int. J. Mach. Tools Man.*, v. 32, 1992, pp. 183-193; Doelves, J., "Electron beam texturing of rolls," *Iron and Steel Eng.*, v. 68, 1991, pp. 33-38; McGeough, J. A., and Rasmussen, H., "A Model for the surface texturing of steel rolls by electrodischarge machining," *Proc. Roy. Soc. Lond.*, Ser. A., v. 436, 1992, pp. 155-164; Boppel, W., "A rapid electron beam engraving process for engraving metal cylinders," *Optik*, v. 77, 1987, pp. 83-92; De Soete, D., "Roll texturing techniques and their implementation at Sidmar," Seminar on the Influence of Surface Roughness in the application of Steel Sheet, Zelzate, Belgium, Oct. 22-23, 1992; and Minamida, K., Suchiro, J., Toshimitu, T., and Kawamoto, T., "Laser system for dulling work roll by Q-switched Nd:YAG laser," *J. Laser Appls.*, v. 1, 1989, pp. 15-20, the entire contents and disclosures of which are hereby incorporated by reference herein. A good general reference for the subject is Mummery, L., *Surface Texture Analysis: The Handbook*, Mühlhausen, Germany, Hommelwerke GmbH, 1990, the entire contents and disclosure of which is hereby incorporated by reference herein. Hector and Sheu, see Hector, L. G., and Sheu, S., "Focused energy beam work roll surface texturing science and technology," *J. Mat. Proc. & Mfg. Sci.*, v. 2, 1993, pp. 63-117, the entire contents and disclosure of which is hereby incorporated by reference herein, discuss the strengths and weaknesses of these approaches. The Nd:YAG laser textures have been discussed in the present invention, since the other approaches are either less beneficial from a tribological standpoint (for plastic deformation or electrical discharge texturing) or are far more expensive. Other such approaches should be considered within the scope of the present invention, and may be useful or beneficial in particular applications.

Figure 6A:
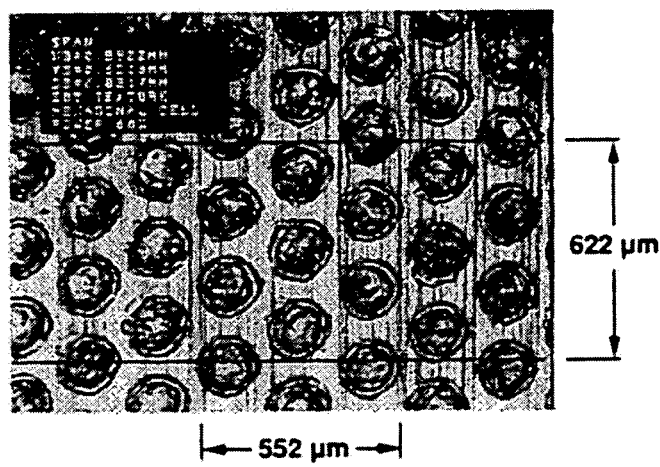
Figure 6B:
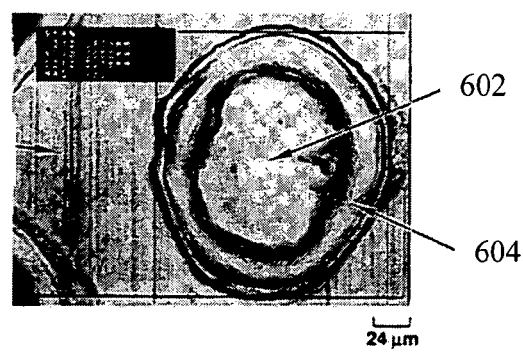
Figure 6B:
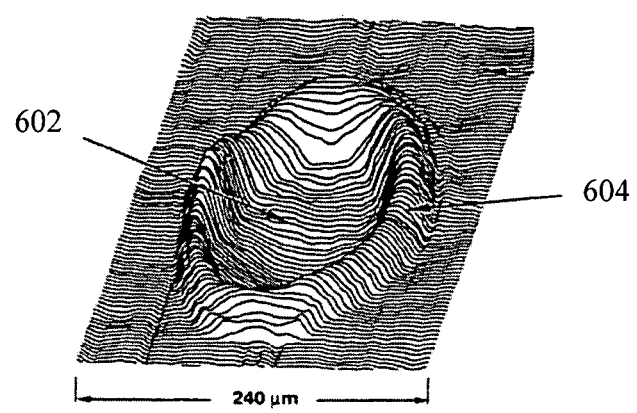

An example of a laser-textured surface finish is shown in FIGS. 6A and 6B. For conventional tribological applications such as hard drives and automotive components such as bearings and cams and tooling applications, the craters 602 produced by a laser serves as a lubricant reservoir, which is entrained and provides lubrication in highly loaded contacts. The crater rim 604 may be removed by a final grinding or chemical-mechanical polishing (CMP) pass, but are beneficial for some applications. For implants, textures with the crater rim 604 removed are desirable. The mechanisms through which the craters 602 prove beneficial are fairly easy to understand; as elastic deformations occur in the contact, the lubricant is displaced and flows outward into the contact. However, conventional laser craters 602 do not provide the beneficial directional properties discussed above.

Directional properties will be discussed again below, but a few benefits of conventionally-textured surfaces should be identified. For metal-on-metal implants, a circumstance where the laser texture serves as pockets of lubricant (synovial fluid) surrounded by areas of intimate metal-on-metal contact would be common. Under load, it is known that the elastic deformations in the metal surfaces may be an order of magnitude larger than the film thickness developed, Hamrock, B. J., *Fundamentals of Fluid Film Lubrication*, New York, McGraw-Hill, 1994, the entire contents and disclosure of which is hereby incorporated by reference herein. When the implant surface deforms elastically, the fluid in the reservoir is extruded into the contact patches, separating them and reducing wear. This mechanism is well-known and is referred to as the percolation theory of lubrication, see Lo, S. W., "A study of flow phenomena in mixed lubrication regime by porous media model," *J. Tribology*, v. 116, 1994, pp. 640-647, the entire contents and disclosure of which is hereby incorporated by reference herein.

For metal-on-plastic implants, the metal may be considered rigid, with significant deformations occurring in the polymer. The polymer extrudes partially into the reservoir, again displacing fluid into the surrounding contact. As sliding occurs, the extruded polymer is not shaved off (via abrasive wear), so the surface slope of the divot or bowl at the surface must be carefully controlled.

Figure 7:
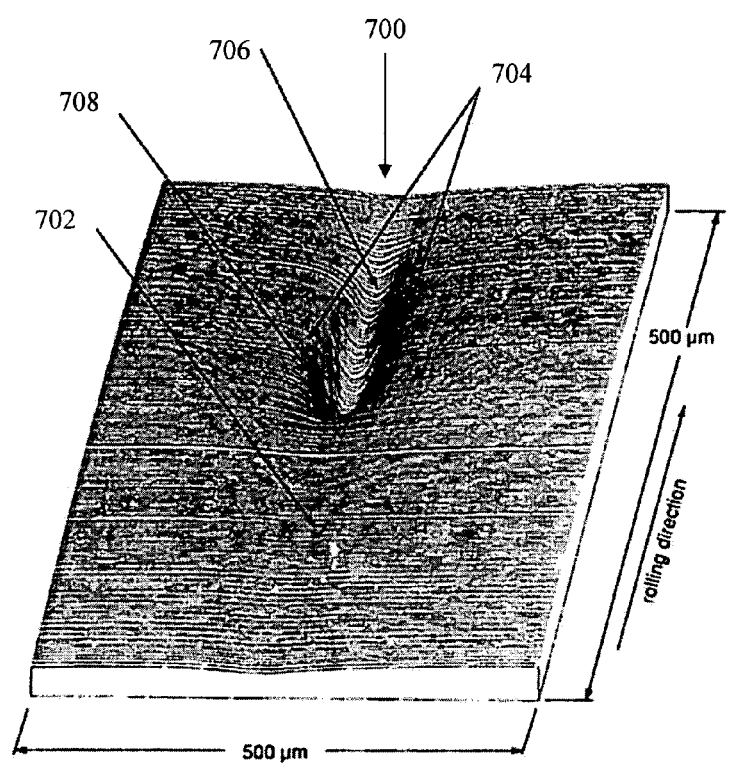
FIG. 7 shows an ovoid bowl produced through inclined laser ablation.

In a series of papers and patents, Hector, Sheu and co-workers developed a technique for preparing what they referred to as ovoid bowls 700 in laser texturing, as shown in FIG. 7, see Hector, L. G., and Sheu, S., "Brightness enhancement with textured roll," U.S. Pat. No. 4,996,113, issued Feb. 26, 1991; Hector, L. G., and Sheu, S., "Focused energy beam work roll surface texturing science and technology," J. Mat. Proc. & Mfg. Sci., v. 2, 1993, pp. 63-117; Hector, L. G., and Sheu, S., "Rolled product with textured surface for improved lubrication, formability and brightness," U.S. Pat. No. 5,250,364, issued Oct. 5, 1993; Hector, L. G., Sheu, S., and Richmond, O., "Tool surface topography for controlling friction and wear in metal-forming processes," J. Tribology, v. 120, 1998, pp. 517-527; Hector, L. G., and Sheu, S., "Enhanced work roll surface texture for cold and hot rolling of aluminum and its alloys," U.S. Pat. No. 5,508,119, issued Apr. 16, 1996; Sheu, S., and Hector, L. G., "Method of providing textures on material by rolling," U.S. Pat. No. 5,025,547, issued Jun. 25, 1991; and Sheu, S., Hector, L. G., and Gorman, J. M., "Sheet product due to massive thickness reduction in last stand of cold rolling," U.S. Pat. No. 5,537,851, issued Jul. 23, 1996, the entire contents and disclosures of which are hereby incorporated by reference herein. These bowls 700 are directional—they present different surface slopes at opposite ends of the bowl 706 and 708, respectively, and two corresponding wall slopes 704—and were demonstrated to be beneficial in rolling of aluminum and other metals. The above-identified patents show that the ovoid, elongated bowls 700 may be prepared by directing the laser at the surface 702 at an inclined angle instead of normally directed as in conventional laser etching. The length of the ovoid bowls in one direction, i.e., in the longest span of the bowls, is approximately 80 to 300 μm. The width of the bowls in a direction perpendicular to the length is approximately 75 to 250 μm. The maximum depth of the bowls is approximately 5 μm. The angle of the shallow region relative to the surface lies at an angle of approximately 5° to 15°. The angle of the deepest region relative to the surface lies at an angle of approximately 16° to 70°. The patents' focus was metal rolling, and they demonstrated that they could reduce abrasive wear (referred to as smudge generation in rolling), adhesive wear (pickup) and friction through use of the materials' textures.

Some of the advantages of the ovoid bowls 700 in metal rolling apply to orthopedics applications as well. For example, if a bowl 700 as shown in FIG. 7 was used on an orthopedic implant, any polymer that extrudes elastically into the bowl 700 may force synovial fluid into the contact, and when sliding against the bowl 700, it may slide against a very gentle surface slope 706 that may not lead to abrasive wear. When sliding in the opposite direction, the polymer may encounter a more aggressive surface 708. The implications are clear—patients who receive a laser textured implant with ovoid bowls 700 forwards, the sliding surface 706 is not aggressive, and rich reservoirs of lubricant may be should not spend a significant amount of time walking backwards. But when walking packed into the surface 702, significantly improving lubricant retention. This has the effect of increasing the film parameter L, with the associated wear and friction benefits as discussed above.

There are numerous indications that additional benefits may be obtained through the presence of reservoirs produced through laser texturing that would greatly improve the artificial implant tribological situation. For example, depressions in the surface are better able to accommodate wear debris, so that delamination or fatigue wear particles are less likely to cause surface damage before they are expelled, see Suh, N., *Tribophysics*, Prentice Hall, 1986, the entire contents and disclosure of which is hereby incorporated by reference herein.

Through proper fixturing and process planning, laser textures allow the production of surfaces such as shown in FIG. 5 (by combining two or three inclined laser ablations), and therefore have the potential to achieve the tribological benefits of engineered surfaces designed for the particular biomechanics of human joints.

Figure 8:
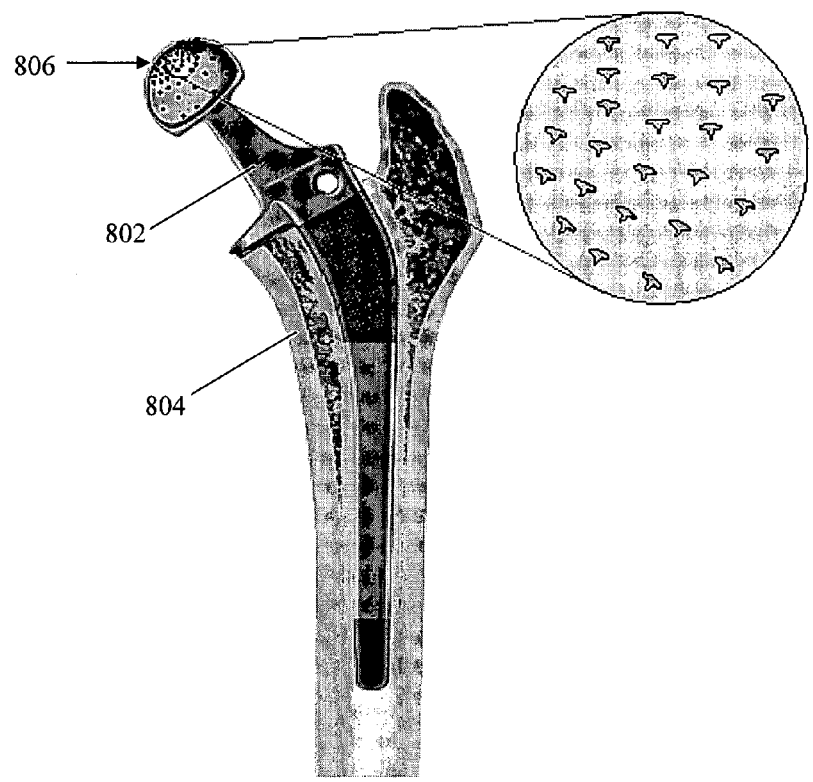
FIG. 8 shows an embodiment of the present invention in which a total hip replacement is depicted as installed in a human femur.

FIG. 8 shows an embodiment of the present invention, in which a total hip replacement 802 is depicted as installed in a human femur 804. The texture 806 is placed on the ball of the hip, and depicted as dots for illustrative purposes—dimples are not normally large enough to be seen at the scale shown in the figure. The reason for including the representation of the dimples is to illustrate that the local spacing and, for that matter, the shape of the dimples, may be modified at different locations in the implant. It should be appreciated that the particular implant application is unimportant. The present invention is suitable for any articulating surface, and ideally suited for wear-prone contacts with a directional loading.

As shown in FIG. 8, in some embodiments, the bearing surface comprises a plurality of regions each comprising a portion of the predetermined pattern of indentations. The plurality of bearing surface regions have at least one different feature of a group of features consisting of: a density of the indentations, an orientation of the indentations and at least one dimension of the indentations. In orthopedic applications, the indentations are placed on the bearing surface in a shape, density and orientation optimized for a particular biomechanical loading.

The above embodiments of the present invention have been described in the context of an orthopedic hip implant application. It should be appreciated, however, that the present invention can be implemented in connection with other orthopedic implants such as orthopedic knee implant, orthopedic shoulder implant, orthopedic elbow implant, orthopedic ankle implant, orthopedic finger implant, orthopedic spine disk implant, and others. It should also be appreciated, however, that the present invention applies to cylinder linings in automotive engines or hydraulic cylinders, golf club heads, cams, and other applications.

As noted, the textured bearing surface has a predetermined pattern constructed and arranged to encourage lubricant entrainment while the bearing surface is under minimal loading, and to restrict lubricant escape from the bearing surface while the bearing surface is under increased loading. In the embodiments described herein, the bearing surface has indentations to form the textured surface.

In some embodiments described above, the indentations each comprise a first leading edge and a first trailing edge that lead and trail the indentation under the increased-loading conditions, and a second leading edge and second trailing edge that lead and train the indentation under the reduced-loading conditions. Although it need not be the case, in many applications, the first leading edge and the second trailing edge are a same edge while the first trailing edge and the second leading edge are a same edge. As noted, the bearing surface is under the increased-loading conditions during relative translation with another bearing surface along a first direction of sliding, and is under the reduced-loading conditions during relative translation with the other bearing surface along a second direction of sliding. In the exemplary application of an orthopedic implant, such first and second sliding directions are substantially opposite each other.

In accordance with certain embodiments of the present invention, the first leading edge is contoured to cause a substantial restriction to flow of said lubricant. Similarly, the second angle is configured to cause a minimum restriction to flow of said lubricant.

As shown in the cross-sectional view of FIG. 5, the indentations 502 are surrounded by plateaus 514, each indentation 502 containing at least one surface 512 that contains a substantially smooth transition to the plateau and whose concavity is zero at the junction 504 with the plateau surface 514. The indentation 502 further comprises a second side 510 that joins plateau surface 514 at point 506 that trails the indentation 502 under reduced-loading conditions. The surface tangent or slope of the first side 512 can be different than that defining the second side 510. In one embodiment, the bearing surface is under reduced-loading during relative translation with another bearing surface along a first direction of sliding 508, and is under increased loading during relative translation against the surface that transitions smoothly to the plateaus 514 along a second direction of sliding.

It should be understood that in some of the above embodiments, the plurality of indentations serve to increase the volume of lubricant contained in the indentations when the plateaus are in contact with an opposing smooth surface, known as the percolation threshold of the surface. In another embodiment, the plurality of indentations serve to contain reservoirs of lubricant, said lubricant being transported into highly loaded conjunctions and then seeping (or percolating) onto plateau surfaces because of elastic deformation of the bearing substrate or extrusion of polymer counter-surface material into the dimple.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An orthopedic implant comprising:
   an articulating textured bearing surface implantable in a patient and configured to undergo unsteady biomechanical loading conditions comprising increased-loading conditions and reduced-loading conditions, said bearing surface having a predetermined pattern of indentations, wherein each indentation comprises a first trailing edge having a contour that encourages lubricant entrainment onto said bearing surface while said bearing surface is under said reduced-loading conditions, and a first leading edge having a contour that is different than the contour of the first trailing edge and that restricts lubricant escape from said bearing surface while said bearing surface is under said increased-loading conditions.

2. The implant of claim 1, wherein said first leading edges of said indentations lead each indentation when said bearing surface undergoes said increased-loading conditions, and wherein said first trailing edges of said indentations trail each indentation when said bearing surface undergoes said reduced-loading conditions, and wherein each said indentation further comprises a second leading edge and a second trailing edge that lead and trail, respectively, each said indentation when said bearing surface undergoes said reduced-loading conditions.

3. The implant of claim 2, wherein said first leading edge and said second trailing edge are a same edge.

4. The implant of claim 2, wherein said first trailing edge and said second leading edge are a same edge.

5. The implant of claim 1, wherein said bearing surface is under said increased-loading conditions during relative translation with another bearing surface along a first direction of sliding, and wherein said bearing surface is under said reduced-loading conditions during relative translation with the other bearing surface along a second direction of sliding.

6. The implant of claim 5, wherein said first leading edge is configured to lead said indentation during said translation in said first sliding direction, and wherein each said indentation comprises a second leading edge configured to lead each said indentation in said second sliding direction and wherein said first leading edge is contoured to cause said lubricant to flow along a first angle between said first sliding direction and a direction of lubricant flow, and wherein said second leading edge is contoured to cause said lubricant to flow along a second angle between said second sliding direction and a direction of lubricant flow.

7. The implant of claim 6, wherein said first angle causes a substantial restriction to flow of said lubricant.

8. The implant of claim 6, wherein said second angle causes a minimum restriction to flow of said lubricant.

9. The implant of claim 1, wherein said orthopedic implant comprises at least one of a group consisting of orthopedic hip implant, orthopedic knee implant, orthopedic shoulder implant, orthopedic elbow implant, orthopedic ankle implant, orthopedic finger implant, and orthopedic spine disk implant.

10. The implant of claim 1, wherein said bearing surface comprises a plurality of regions each comprising a portion of said pattern of indentations.

11. The implant of claim 10, wherein said plurality of bearing surface regions have at least one different feature of a group of features consisting of: a density of said indentations, an orientation of said indentations and at least one dimension of said indentations.

12. The implant of claim 1, wherein said lubricant is synovial fluid.

13. The implant of claim 1, wherein said indentations are placed on said bearing surface in a shape, density and orientation optimized for a particular biomechanical loading.

14. The implant of claim 1, wherein said textured bearing surface is formed by at least one of a group consisting of: laser texturing, chemical etching, plasma etching, electrical discharge machining, electron beam machining and peening.

15. The implant of claim 1, wherein a substantial portion of said indentations are ovoid dimples.

16. The implant of claim 1, wherein said pattern of indentations increases the volume of lubricant contained on said bearing surface when plateaus surrounding said indentations are in contact with an opposing smooth surface.

17. The implant of claim 1, wherein said indentations are configured to contain reservoirs of lubricant, said lubricant being transported into highly loaded conjunctions and then seeping or percolating onto plateau surfaces surrounding said indentations in response to elastic deformation of said bearing.

18. The implant of claim 1, wherein the indentations are dimensioned to receive and contain debris.

19. An orthopedic implant comprising:
an articulating textured bearing surface implantable in a patient and configured to undergo unsteady biomechanical conditions comprising increased-loading conditions and reduced-loading conditions, said bearing surface having a predetermined matrix pattern of indentations and surrounding plateaus, each said indentation having at least one surface that contains a substantially smooth transition to the plateau and whose concavity is zero at the junction with the plateau surface in order to encourage lubricant entrainment onto said bearing surface while said bearing surface is under said reduced-loading conditions.

20. The implant of claim 19, wherein each said indentation further comprises a second surface that trails said indentation under said reduced-loading conditions.

21. The implant of claim 20, wherein said at least one surface leads said indentation during said reduced-loading conditions, and said second surface leads said indentation during said increased-loading conditions.

22. The implant of claim 19, wherein said bearing surface is under said reduced-loading conditions during relative translation with another bearing surface along a first direction of sliding, and wherein said bearing surface is under said increased-loading conditions during relative translation with the other bearing surface along a second direction of sliding.

23. The implant of claim 19, wherein said orthopedic implant comprises at least one of a group consisting of orthopedic hip implant, orthopedic knee implant, orthopedic shoulder implant, orthopedic elbow implant, orthopedic ankle implant, orthopedic finger implant, and orthopedic spine disk implant.

24. The implant of claim 19, wherein said bearing surface comprises a plurality of regions each comprising a portion of said pattern of indentations.

25. The implant of claim 24, wherein said plurality of bearing surface regions have at least one different feature of a group of features consisting of: a density of said indentations, an orientation of said indentations and at least one dimension of said indentations.

26. The implant of claim 19, wherein said indentations are placed on said bearing surface in a density and orientation optimized for particular unsteady loading conditions.

27. The implant of claim 19, wherein said indentations are placed on said bearing surface in a density and orientation optimized for a particular biomechanical loading.

28. The implant of claim 19, wherein said textured bearing surface is formed by at least one of a group consisting of: laser texturing, chemical etching, plasma etching, electrical discharge machining, electron beam machining and peening.

29. The implant of claim 19, wherein a substantial portion of said plurality of indentations are ovoid dimples.

30. The orthopedic implant of claim 19, wherein the plurality of indentations serve to increase the volume of lubricant contained on said bearing surface when plateaus surrounding said indentations are in contact with an opposing smooth surface.

31. The implant of claim 19, wherein said indentations are configured to contain reservoirs of lubricant, said lubricant being transported into highly loaded conjunctions and then seeping or percolating onto said plateau surfaces surrounding said indentations in response to elastic deformation of said bearing surface or polymer extrusion into the reservoir.

32. The implant of claim 19, wherein the indentations are dimensioned to receive and contain debris.

33. An orthopedic implant comprising:
an articulating surface implantable in a patient; and
a plurality of dimples each having a first surface slope and an opposing second surface slope, wherein the first surface slope is steeper than the second surface slope, and wherein the dimples are arranged on the articulating surface such that each of the first surface slopes are oriented substantially towards a direction of increased loading so that the first surface slope restricts lubricant escape from the bearing surface while the bearing surface is under increased-loading conditions, and the second surface slope encourages encourage lubricant entrainment onto the bearing surface while the articulating surface is under reduced-loading conditions.

34. The implant of claim 33, wherein the second surface slopes are oriented substantially towards a direction of reduced-loading opposed to the direction of increased loading.

35. The implant of claim 33, wherein orthopedic implant is a hip replacement.

36. The implant of claim 35, wherein the hip replacement comprises a ball and socket, and wherein the articulating surface is on a ball of the hip replacement.

37. The implant of claim 33, wherein each of the plurality of dimples is wider at the first surface slope than the second surface slope.

38. The implant of claim 33, wherein the first surface slope is at an angle of approximately 16° to 70°.

39. The implant of claim 33, wherein the second surface slope is at an angle of approximately 5° to 15°.

40. The implant of claim 33, wherein each of the plurality of dimples has of depth of approximately 5 µm.

41. The implant of claim 33, wherein one or more plateaus on the articulating surface separate the plurality of dimples.

42. The implant of claim 33, wherein each of the plurality of dimples is a reservoir for lubricant.

43. The implant of claim 33, wherein each of the plurality of dimples is an ovoid dimple.

44. An orthopedic implant comprising:
an articulating bearing surface implantable in a patient and configured to undergo unsteady biomechanical loading conditions comprising increased-loading conditions and reduced-loading conditions, said bearing surface comprising a plurality of dimples each having means for encouraging lubricant entrainment onto said bearing surface while said bearing surface is under said reduced-loading conditions, and means for restricting lubricant escape from said bearing surface while said bearing surface is under said increased-loading conditions.

45. The implant of claim 44, wherein said means for restricting lubricant escape from said bearing surface while said bearing surface is under said increased-loading conditions comprises a first leading edge configured to lead each said indentation when said bearing surface undergoes said increased-loading conditions.

46. The implant of claim 45, wherein said means for encouraging lubricant entrainment onto said bearing surface while said bearing surface is under said reduced-loading conditions comprises a first trailing edge configured to trail each said indentation when said bearing surface undergoes said reduced-loading conditions.

47. The implant of claim 44, wherein each said indentation comprises a first surface slope oriented substantially towards said direction of increased-loading conditions and an opposing second surface slope, wherein the first surface slope is steeper than the second surface slope, and wherein said means for encouraging lubricant entrainment onto said bearing surface while said bearing surface is under said reduced-loading conditions comprises said second surface slope.

48. The implant of claim 47, means for restricting lubricant escape from said bearing surface while said bearing surface is under said increased-loading conditions comprises said first surface slope.

49. The implant of claim 44, wherein each said indentation comprises at least one surface having a substantially smooth transition to a plateau surface surrounding said indentations, said at least one surface having concavity of said at least one surface is zero at the junction with said plateau surface, wherein said means for encouraging lubricant entrainment onto said bearing surface while said bearing surface is under said reduced-loading conditions comprises said at least one surface.

50. The implant of claim 44, wherein said bearing surface is under said increased-loading conditions during relative translation with another bearing surface along a first direction of sliding, and wherein said bearing surface is under said reduced-loading conditions during relative translation with the other bearing surface along a second direction of sliding.

* * * * *